(12) United States Patent
Johnston

(10) Patent No.: US 7,608,842 B2
(45) Date of Patent: Oct. 27, 2009

(54) DRIVING SCANNING FIBER DEVICES WITH VARIABLE FREQUENCY DRIVE SIGNALS

(75) Inventor: Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 272 days.

(21) Appl. No.: 11/796,275

(22) Filed: Apr. 26, 2007

(65) Prior Publication Data

US 2008/0265178 A1 Oct. 30, 2008

(51) Int. Cl.
*A61N 5/00* (2006.01)

(52) U.S. Cl. ............ 250/492.1; 250/491.1; 850/1; 850/5; 850/6; 600/101; 600/160; 600/182; 600/407; 600/478; 385/25; 385/116; 385/117; 385/147; 356/477; 356/479

(58) Field of Classification Search ............ 250/492.1, 250/491.1; 385/25, 116, 117, 147; 356/196, 356/477, 479; 850/1, 5, 6; 600/101, 160, 600/182, 407, 478
See application file for complete search history.

(56) References Cited

U.S. PATENT DOCUMENTS

| | | |
|---|---|---|
| 3,470,320 A | 9/1969 | Pike et al. |
| 3,644,725 A | 2/1972 | Lochridge, Jr. |
| 4,206,495 A | 6/1980 | McCaslin |
| 4,234,788 A | 11/1980 | Palmer et al. |
| 4,264,208 A | 4/1981 | Haberl et al. |
| 4,710,619 A | 12/1987 | Haberl |
| 4,743,283 A | 5/1988 | Borsuk |
| 4,768,513 A | 9/1988 | Suzuki |
| 4,770,185 A | 9/1988 | Silverstein et al. |
| 4,782,228 A | 11/1988 | Westell |
| 4,821,117 A | 4/1989 | Sekiguchi et al. |
| 4,831,370 A | 5/1989 | Smoot |
| 4,872,458 A | 10/1989 | Kanehira et al. |

(Continued)

FOREIGN PATENT DOCUMENTS

EP 1077360 2/2001

(Continued)

OTHER PUBLICATIONS

Brown, Christopher M., et al., "Optomechanical design and fabrication of resonant microscanners for a scanning fiber endoscope", *Optical Engineering*, vol. 45, XP002469237, (Apr. 2006), pp. 1-10.

(Continued)

*Primary Examiner*—David A Vanore
*Assistant Examiner*—Michael J Logie
(74) *Attorney, Agent, or Firm*—Blakely Sokoloff Taylor & Zafman LLP

(57) ABSTRACT

Methods of moving or vibrating cantilevered optical fibers of scanning fiber devices are disclosed. In one aspect, a method may include vibrating the cantilevered optical fiber at an initial frequency that is substantially displaced from a resonant frequency of the cantilevered optical fiber. Then, the frequency of vibration of the cantilevered optical fiber may be changed over a period of time toward the resonant frequency. Light may be directed through an end of the cantilevered optical fiber while the cantilevered optical fiber is vibrated.

32 Claims, 8 Drawing Sheets

U.S. PATENT DOCUMENTS

| | | | |
|---|---|---|---|
| 4,948,219 A | 8/1990 | Seino et al. | |
| 4,963,018 A | 10/1990 | West | |
| 5,081,350 A | 1/1992 | Iwasaki et al. | |
| 5,172,685 A | 12/1992 | Nudelman | |
| 5,178,130 A | 1/1993 | Kaiya | |
| 5,185,835 A | 2/1993 | Vial et al. | |
| 5,315,383 A | 5/1994 | Yabe et al. | |
| 5,360,968 A | 11/1994 | Scott | |
| 5,454,807 A | 10/1995 | Lennox et al. | |
| 5,455,669 A | 10/1995 | Wetteborn | |
| 5,459,570 A | 10/1995 | Swanson et al. | |
| 5,557,444 A | 9/1996 | Melville et al. | |
| 5,596,339 A | 1/1997 | Furness, III et al. | |
| 5,627,922 A | 5/1997 | Kopelman et al. | |
| 5,664,043 A | 9/1997 | Donaldson et al. | |
| 5,694,237 A | 12/1997 | Melville | |
| 5,695,491 A | 12/1997 | Silverstein | |
| 5,701,132 A | 12/1997 | Kollin et al. | |
| 5,751,465 A | 5/1998 | Melville et al. | |
| 5,784,098 A | 7/1998 | Shoji et al. | |
| 5,822,073 A | 10/1998 | Yee et al. | |
| 5,822,486 A | 10/1998 | Svetkoff et al. | |
| 5,887,009 A * | 3/1999 | Mandella et al. | 372/6 |
| 5,894,122 A | 4/1999 | Tomita | |
| 5,903,397 A | 5/1999 | Melville et al. | |
| 5,913,591 A | 6/1999 | Melville | |
| 5,939,709 A | 8/1999 | Ghislain et al. | |
| 5,969,871 A | 10/1999 | Tidwell et al. | |
| 5,982,528 A | 11/1999 | Melville | |
| 5,982,555 A | 11/1999 | Melville et al. | |
| 5,991,048 A | 11/1999 | Karlson et al. | |
| 5,995,264 A | 11/1999 | Melville | |
| 6,046,720 A | 4/2000 | Melville et al. | |
| 6,049,407 A | 4/2000 | Melville | |
| 6,061,163 A | 5/2000 | Melville | |
| 6,069,698 A | 5/2000 | Ozawa et al. | |
| 6,069,725 A | 5/2000 | Melville | |
| 6,097,353 A | 8/2000 | Melville et al. | |
| 6,154,321 A | 11/2000 | Melville et al. | |
| 6,157,352 A | 12/2000 | Kollin et al. | |
| 6,166,841 A | 12/2000 | Melville | |
| 6,191,761 B1 | 2/2001 | Melville et al. | |
| 6,204,832 B1 | 3/2001 | Melville et al. | |
| 6,220,711 B1 | 4/2001 | Melville et al. | |
| 6,243,186 B1 | 6/2001 | Melville et al. | |
| 6,257,727 B1 | 7/2001 | Melville | |
| 6,263,234 B1 | 7/2001 | Engelhardt et al. | |
| 6,281,862 B1 | 8/2001 | Tidwell et al. | |
| 6,285,505 B1 | 9/2001 | Melville et al. | |
| 6,288,816 B1 | 9/2001 | Melville et al. | |
| 6,291,819 B1 | 9/2001 | Hartley | |
| 6,294,775 B1 * | 9/2001 | Seibel et al. | 250/208.1 |
| 6,317,548 B1 | 11/2001 | Rockwell et al. | |
| 6,369,953 B2 | 4/2002 | Melville et al. | |
| 6,388,641 B2 | 5/2002 | Tidwell et al. | |
| 6,411,838 B1 | 6/2002 | Nordstrom et al. | |
| 6,441,359 B1 | 8/2002 | Cozier et al. | |
| 6,492,962 B2 | 12/2002 | Melville et al. | |
| 6,535,183 B2 | 3/2003 | Melville et al. | |
| 6,538,625 B2 | 3/2003 | Tidwell et al. | |
| 6,560,028 B2 | 5/2003 | Melville et al. | |
| 6,563,105 B2 | 5/2003 | Seibel et al. | |
| 6,581,445 B1 | 6/2003 | Weiss | |
| 6,700,552 B2 | 3/2004 | Kollin et al. | |
| 6,734,835 B2 | 5/2004 | Tidwell et al. | |
| 6,747,753 B1 | 6/2004 | Yamamoto | |
| 6,845,190 B1 * | 1/2005 | Smithwick et al. | 385/25 |
| 6,850,673 B2 | 2/2005 | Johnston, II et al. | |
| 6,856,712 B2 * | 2/2005 | Fauver et al. | 385/12 |
| 6,867,753 B2 | 3/2005 | Chinthammit et al. | |
| 6,959,130 B2 | 10/2005 | Fauver et al. | |
| 6,975,898 B2 | 12/2005 | Seibel | |
| 6,977,631 B2 | 12/2005 | Melville et al. | |
| 7,068,878 B2 | 6/2006 | Crossman-Bosworth et al. | |
| 7,123,790 B2 | 10/2006 | Rosman et al. | |
| 7,159,782 B2 | 1/2007 | Johnston et al. | |
| 7,184,150 B2 | 2/2007 | Qualing et al. | |
| 7,189,961 B2 | 3/2007 | Johnston et al. | |
| 7,230,583 B2 | 6/2007 | Tidwell et al. | |
| 7,252,236 B2 | 8/2007 | Johnston et al. | |
| 2001/0051761 A1 | 12/2001 | Khadem | |
| 2001/0055462 A1 * | 12/2001 | Seibel | 385/147 |
| 2002/0062061 A1 | 5/2002 | Kaneko et al. | |
| 2002/0064341 A1 * | 5/2002 | Fauver et al. | 385/25 |
| 2002/0080359 A1 | 6/2002 | Denk et al. | |
| 2002/0093467 A1 | 7/2002 | Tidwell et al. | |
| 2002/0093563 A1 | 7/2002 | Cline et al. | |
| 2002/0097498 A1 | 7/2002 | Melville et al. | |
| 2002/0139920 A1 | 10/2002 | Seibel et al. | |
| 2003/0004412 A1 * | 1/2003 | Izatt et al. | 600/425 |
| 2003/0010825 A1 | 1/2003 | Schmidt et al. | |
| 2003/0010826 A1 | 1/2003 | Dvorkis et al. | |
| 2003/0016187 A1 | 1/2003 | Melville et al. | |
| 2003/0048540 A1 | 3/2003 | Xie et al. | |
| 2003/0142042 A1 | 7/2003 | Tidwell et al. | |
| 2003/0169966 A1 | 9/2003 | Tokizaki | |
| 2003/0202361 A1 | 10/2003 | Johnston et al. | |
| 2004/0061072 A1 | 4/2004 | Gu et al. | |
| 2004/0122328 A1 | 6/2004 | Wang et al. | |
| 2004/0153030 A1 | 8/2004 | Novak et al. | |
| 2004/0196213 A1 | 10/2004 | Tidwell et al. | |
| 2004/0212851 A1 | 10/2004 | Osakabe | |
| 2004/0254474 A1 * | 12/2004 | Seibel et al. | 600/473 |
| 2005/0020926 A1 | 1/2005 | Wiklof et al. | |
| 2005/0025368 A1 | 2/2005 | Glukhovsky | |
| 2005/0085708 A1 | 4/2005 | Fauver et al. | |
| 2005/0085721 A1 | 4/2005 | Fauver et al. | |
| 2005/0174610 A1 | 8/2005 | Fukawa | |
| 2005/0182295 A1 | 8/2005 | Soper et al. | |
| 2005/0238277 A1 | 10/2005 | Wang et al. | |
| 2006/0072189 A1 | 4/2006 | DiMarzio | |
| 2006/0072843 A1 | 4/2006 | Johnston | |
| 2006/0072874 A1 * | 4/2006 | Johnston | 385/25 |
| 2006/0077121 A1 | 4/2006 | Melville et al. | |
| 2006/0138238 A1 | 6/2006 | Johnston et al. | |
| 2006/0149134 A1 | 7/2006 | Soper et al. | |
| 2006/0186325 A1 * | 8/2006 | Johnston et al. | 250/234 |
| 2006/0195014 A1 | 8/2006 | Seibel et al. | |
| 2006/0226231 A1 | 10/2006 | Johnston et al. | |
| 2006/0287647 A1 | 12/2006 | Torchia et al. | |
| 2007/0081168 A1 | 4/2007 | Johnston et al. | |
| 2007/0091426 A1 | 4/2007 | Johnston et al. | |
| 2007/0129601 A1 | 6/2007 | Johnston et al. | |
| 2007/0156021 A1 | 7/2007 | Morse et al. | |
| 2007/0273930 A1 | 11/2007 | Berier et al. | |

FOREIGN PATENT DOCUMENTS

| | | |
|---|---|---|
| EP | 1360927 | 11/2003 |
| EP | 1864606 | 12/2007 |
| GB | 2057709 | 4/1981 |
| GB | 2378259 | 2/2003 |
| WO | WO-9300551 | 1/1993 |
| WO | WO-0174266 | 10/2001 |
| WO | GB2378259 | 2/2003 |
| WO | WO-03019661 | 3/2003 |
| WO | WO-2004/040267 | 5/2004 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO2006041459 * | 4/2006 |
| WO | WO-2006041459 | 4/2006 |

| WO | WO-2006071216 | 7/2006 |
| WO | WO-2006096155 | 9/2006 |
| WO | WO-2006/106853 | 10/2006 |
| WO | WO-2006104489 | 10/2006 |
| WO | WO-200612480 | 11/2006 |
| WO | EP1864606 | 12/2006 |
| WO | WO-2007070831 | 6/2007 |
| WO | WO-2008/033168 | 3/2008 |

OTHER PUBLICATIONS

Smithwick, Y. J., et al., "An error space controller for a resonating fiber scanner: simulation and implementation", *Journal of Dynamic Systems, Measurement and Control*, Fairfiled, N.J., U.S., vol. 128, No. 4, XP009095153, ISSN: 0022-0434, (Dec. 2006), pp. 899-913.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory, University of Washington*, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition, BED*-vol. 51, (Nov. 11-16, 2001), 165-166.

Chen, Tailian, et al., "Experiment of Coalescence of Dual Bubbles on Micro Heaters", *Department of Mechanical Engineering, University of Florida*, Gainesville, FL 32611-6300. USA., Printed from the Internet Aug. 13, 2006, 1-10.

Fauver, Mark, et al., "Microfabrication of fiber optic scanners", (2002) *In Proceedings of Optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616, (Oct. 13, 2004), 173-179.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE* vol. 4957, (2003), 46-55.

Seibel, Eric J., et al., "Modeling optical fiber dynamics for increased efficiencies in scanning fiber applications", *Optical Fibers and Sensors for Medical Applications V, proceedings of SPIE* vol. 5691, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", *Optial Fibers and Sensors for Medical Applications II, Proc. of SPIE*, vol. 4616, (2002), 1-7.

Seibel, Eric J., et al., "Single fiber flexible endocope: general design for small size, high resoljution, and wide field of view", *Human Interface Technology Laboratory, College of Engineering, University of Washington*, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), P-178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", *2000 Annual Fall Meeting Abstracts T4.57*, (2000), 1.

Smithwick, Quinn Y., et al., "54.3: Modeling and Control of the Resonant Fiber Scanner for Laser Scanning Display or Acquisition", *Department of Aeronautics and Astronautics, University of Washington*, Seattle, WA SID 03 Digest, (2003), 1455-1457.

Smithwick, Quinn Y., et al., "A Nonlinear State-Space Model of a Resonating Single Fiber Scanner for Tracking Control: Theory and Experiment", *Transactions fo the ASME*, vol. 126, (Mar. 2004), 88-101.

Smithwick, Quinn Y., et al., "Control Aspects of the Single Fiber Scanning Endoscope", (2001) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory, University of Washington*, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE* vol. 6083., (2006), 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE* vol. 4876 (2003), (2003), 72-83.

Wang, Wei-Chih, et al., "Micromachined opital waveguide cantilever as a resonant optical scanner", *Department of Mechanical Engineering, University of Washington*, Seattle, WA 98195, *Sensors and Actuators A 102*, (2002), 165-175.

"PCT/US2007/011480 International Search Report", (Feb. 6, 2008), 3 pages.

"PCT/US2007/009598 International Search Report", (Jan. 3, 2008), 3 pages.

* cited by examiner

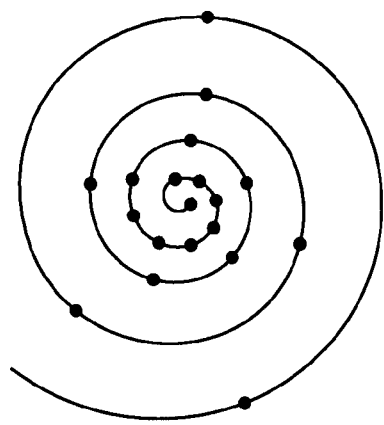
FIG. 5
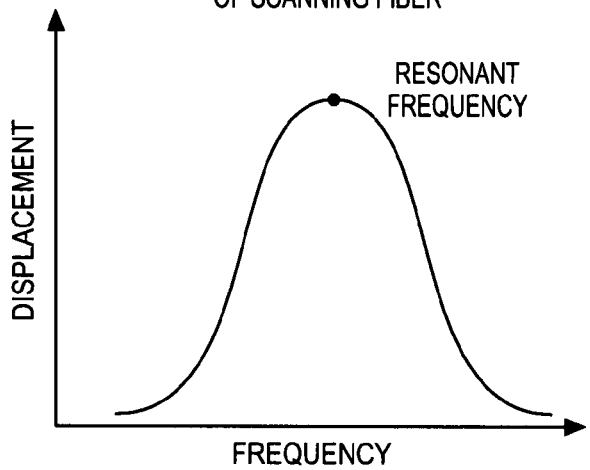
FIG. 6
METHOD OF ACTUATING
CANTILEVERED OPTICAL FIBER
730
VIBRATE CANTILEVERED OPTICAL FIBER AT INITIAL FREQUENCY THAT IS SUBSTANTIALLY DISPLACED FROM RESONANT FREQUENCY OF CANTILEVERED OPTICAL FIBER —731
↓
CHANGE FREQUENCY OF VIBRATION OF CANTILEVERED OPTICAL FIBER OVER PERIOD OF TIME TOWARD RESONANT FREQUENCY —732
FIG. 7

DRIVING SCANNING FIBER DEVICES WITH VARIABLE FREQUENCY DRIVE SIGNALS

BACKGROUND

1. Field

Embodiments of the invention relate to scanning fiber devices. In particular, embodiments of the invention relate to actuating or vibrating cantilevered optical fibers of scanning fiber devices.

2. Background Information

Scanning fiber devices commonly include a single, cantilevered optical fiber that may be vibrated or scanned in one or two dimensions in a scan pattern to construct an image. The cantilevered optical fiber is commonly vibrated at or very near its mechanical or vibratory resonant frequency.

BRIEF DESCRIPTION OF THE SEVERAL VIEWS OF THE DRAWINGS

The invention may best be understood by referring to the following description and accompanying drawings that are used to illustrate embodiments of the invention. In the drawings:

FIG. 5 conceptually illustrates that oversampling may occur in the center portions of a spiral scan pattern generated with constant frequency, increasing amplitude actuator drive signals like those shown in FIG. 4 if backscattered light from the illumination spot is sampled at a constant rate.

FIG. 6 is a graph of resonant gain characteristics of a cantilevered optical fiber operated in a first mode of resonance.

FIG. 7 is a block diagram of a method of actuating a cantilevered optical fiber of a scanning fiber device, according to embodiments of the invention.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1:
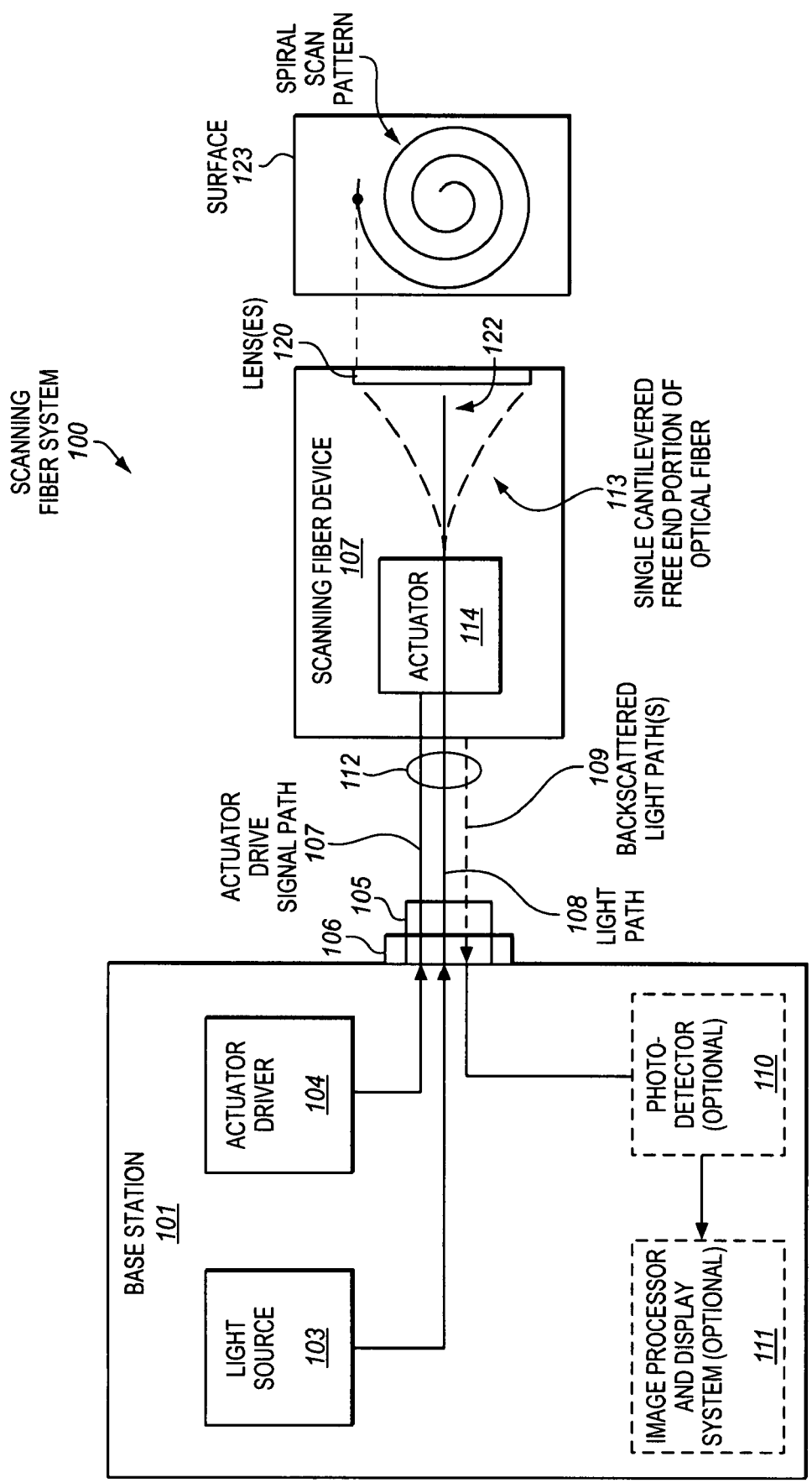
FIG. 1 is a block diagram of an example scanning fiber system, according to embodiments of the invention.

FIG. 1 is a block diagram of an example scanning fiber system 100, according to embodiments of the invention. In various embodiments of the invention, the scanning fiber system may take the form of a scanning fiber endoscope, scanning fiber boroscope, scanning fiber microscope, other type of scanning fiber scope, scanning fiber bar code reader, scanning fiber image display device, or other scanning fiber image acquisition and/or display device known in the art.

As is known, endoscopes represent instruments or devices to be inserted into a patient to look inside a body cavity, lumen, or otherwise look inside the patient. Examples of suitable types of endoscopes include, but are not limited to, bronchoscopes, colonoscopes, gastroscopes, duodenoscopes, sigmoidoscopes, thorascopes, ureteroscopes, sinuscopes, boroscopes, and thorascopes, to name just a few examples.

The scanning fiber system has a two-part form factor that includes a base station 101 and a scanning fiber device 102, although such a two-part form factor is not required. The scanning fiber device is electrically and optically coupled with the base station through one or more cables 112. In particular, the scanning fiber device includes a connector 105 to connect or mate with a corresponding connector interface 106 of the base station.

The base station includes a light source 103 to provide light to the scanning fiber device through a light path 108. Examples of suitable light sources include, but are not limited to, lasers, laser diodes, vertical cavity surface-emitting lasers (VCSELs), light-emitting diodes (LEDs), other light emitting devices known in the arts, and combinations thereof. In various example embodiments of the invention, the light source may include a red light source, a blue light source, a green light source, an RGB light source, a white light source, an infrared light source, an ultraviolet light source, a high intensity therapeutic laser light source, or a combination thereof. Depending on the particular implementation, the light source may emit a continuous stream of light, modulated light, or a stream of light pulses.

The base station also includes an actuator driver 104 to provide electrical signals, referred to herein as actuator drive signals, to the scanning fiber device through an actuator drive signal path 107. The actuator driver may be implemented in hardware (for example a circuit), software (for example a routine or program), or a combination of hardware and software.

In one or more embodiments of the invention, the actuator driver may include one or more lookup tables or other data structures stored in a memory that may provide actuation drive signal values. By way of example, the actuation drive signal values may be ideal values that are adjusted based on calibration. One suitable type of calibration is described in U.S. Patent Application 20060072843, entitled "REMAPPING METHODS TO REDUCE DISTORTIONS IN IMAGES", by Richard S. Johnston. Other calibration approaches are also suitable. Alternatively, the actuator driver may include a processor, ASIC, or other circuit to compute the actuation drive signal values in real time. As another option, computation may be used to interpolate between stored values. The actuator driver may cycle through the lookup tables or computations providing the values. The values may be digital and may be provided to a digital-to-analog converter of the actuator driver. The actuator driver may also include one or more amplifiers to amplify the analog version of the actuator drive signals. These are just a few illustrative examples of suitable actuator drivers.

The scanning fiber device 102 includes a single cantilevered optical fiber 113 and an actuator 114 to actuate or move the cantilevered optical fiber. Examples of suitable types of actuators include, but are not limited to, piezoelectric tubes, Electroactive Polymer (EAP) tubes, other actuator tubes, other piezoelectric actuators, other EAP actuators, magnetic actuators, electromagnetic actuators, electrostatic actuators, sonic actuators, electroacoustic actuators, electromechanical actuators, microelectromechanical systems (MEMS), and other transducers capable of moving the cantilevered optical fiber.

The actuator may receive the actuator drive signals. The actuator may actuate or move the cantilevered optical fiber based on, and responsive to, the received actuator drive signals. In embodiments of the invention, the actuator drive signals may cause the actuator to move the cantilevered optical fiber in a scan pattern. Suitable two-dimensional scan patterns include, but are not limited to, circular or oval spiral scan patterns, and other expanding scan patterns.

The cantilevered optical fiber may receive the light from the light source. The light may be emitted from, or otherwise directed through, a distal end or tip 122 of the cantilevered optical fiber, while the optical fiber is moved in the scan pattern. The emitted light may be passed through one or more lenses 120 to generate a focused beam or illumination spot that may be moved across a surface 123 in the scan pattern. In the illustration, a spiral scan pattern is shown and a dot shows a position of the illumination spot at a particular point in time during the scan.

The scanning fiber device may be used to construct an image. Constructing an image may include displaying or forming an image on the surface and/or acquiring an image of the surface. In displaying the image on the surface, the light emitted from the end of the optical fiber may be modulated during the scan depending on position and generally passed through a lens system in order to form a desired image on the surface. In acquiring the image of the surface, the scanning fiber device may scan the illumination spot through the lens system and over the surface in the scan. Backscattered light may be captured in time series and used to construct an image.

Different ways of collecting the backscattered light are possible. As shown, one or more optical fibers, or other backscattered light paths 109, may optionally be included to collect and convey backscattered light back to one or more optional photodetectors 110 of the base station. Alternatively, the scanning fiber device may optionally include photodetectors proximate a distal tip thereof. The base station may also include an optional image processing and display system 111 to generate and display images based on light detected by the photodetectors. It should be noted that the collection and detection of backscattered light is generally omitted in an image display device.

A simplified base station has been shown and described in order to avoid obscuring the description. It is to be appreciated that the base station may include other components. Representative components that may be included in the base station include, but are not limited to, a power source, a user interface, a memory, and the like. Furthermore, the base station may include supporting components like clocks, amplifiers, digital-to-analog converters, analog-to-digital converters, and the like.

Figure 2:
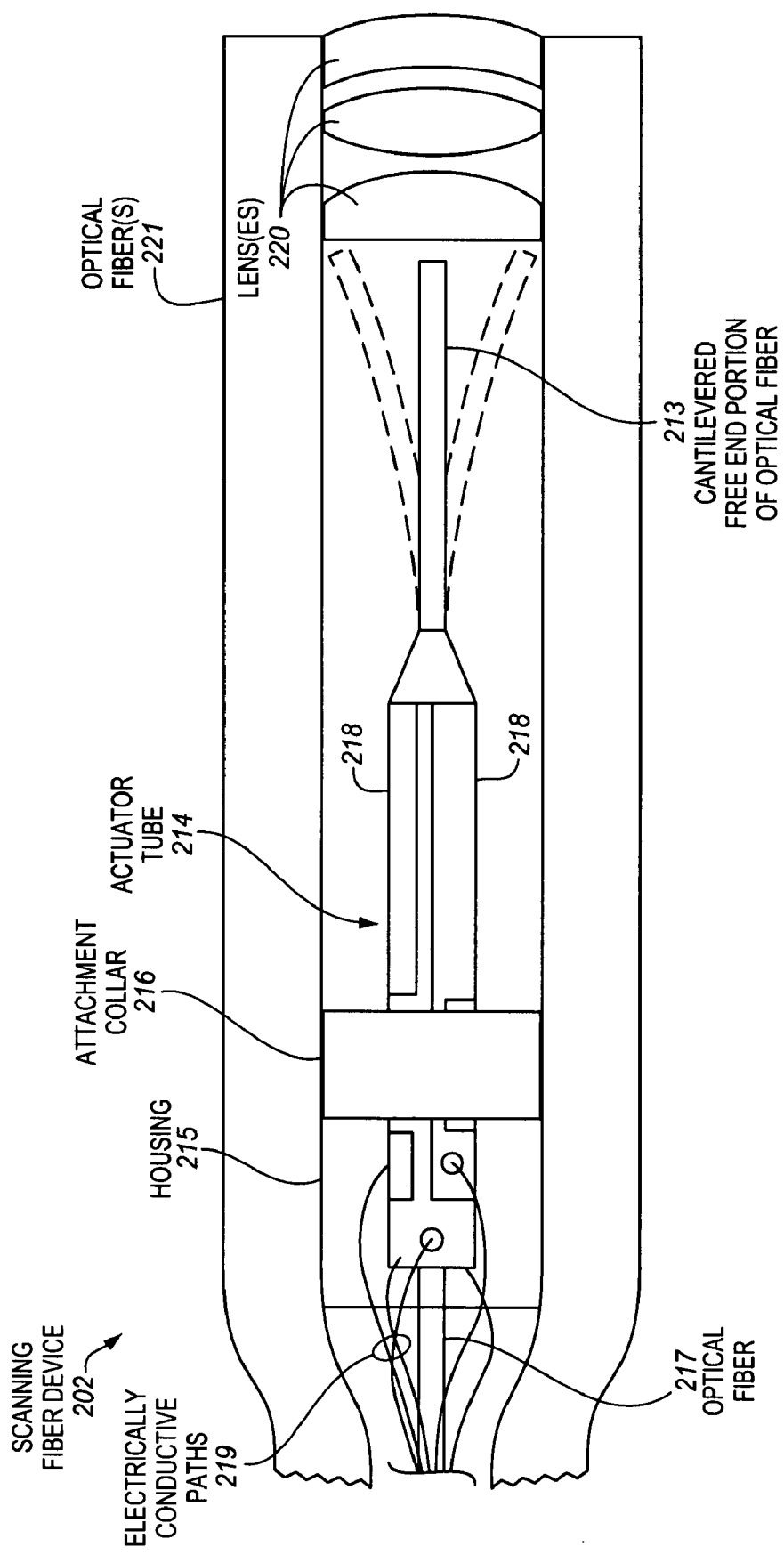
FIG. 2 is a cross-sectional side view of one example of a suitable scanning fiber device, according to one or more embodiments of the invention.

FIG. 2 is a cross-sectional side view of one example of a suitable scanning fiber device 202, according to one or more embodiments of the invention. This particular scanning fiber device is well suited for use as an endoscope or other relatively small device, although in other implementations the design and operation may vary considerably. The scope of the invention is not limited to this particular device.

The scanning fiber device includes a housing 215. In one or more embodiments, the housing may be relatively small and hermetically sealed. For example, the housing may be generally tubular, have a diameter that is about 5 millimeters (mm) or less, and have a length that is about 20 mm or less. The housing typically includes one or more lenses 220. Examples of suitable lenses include those manufactured by Pentax Corporation, although other lenses may optionally be used.

An actuator tube 214 is included in the housing and attached to the housing with an attachment collar 216. In one or more embodiments of the invention, the actuator tube may include a piezoelectric tube, such as, for example, of a PZT 5A material, although this is not required. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass. The actuator tube may be inserted through a tightly fitting generally cylindrical opening of the attachment collar.

A portion of a single optical fiber 217 is inserted through a generally cylindrical opening in the actuator tube. A cantilevered free end portion 213 of the optical fiber extends beyond an end of the actuator tube within the housing and may be attached to the end of the actuator tube. Other configurations are also possible. The cantilevered optical fiber is flexible and may be vibrated or moved by the actuator.

The actuator tube has electrodes 218 thereon. Wires or other electrically conductive paths 219 are electrically coupled with the electrodes to convey actuator drive signals to the electrodes. In one example embodiment of the invention, the actuator tube may include a piezoelectric tube having four, quadrant metal electrodes on an outer surface thereof to move the cantilevered optical fiber in two dimensions. Four paths may each be soldered to, or otherwise electrically coupled with, respective ones of the four electrodes. Responsive to the actuator drive signals, the four electrodes may cause the piezoelectric tube to vibrate or move the optical fiber in a two-dimensional scan pattern. Alternatively, two orthogonal electrodes may optionally be used. In one or more embodiments, the piezoelectric tube may have an optional ground electrode on an inside surface thereof.

As shown, in one or more embodiments, one or more optical fibers 221 may optionally be included around the outside of the housing to collect and convey backscattered light from the illumination spot back to one or more photodetectors, for example located in the base station. Alternatively, one or more photodetectors may be included at a distal tip of the scanning fiber device, or omitted entirely.

There are different ways to drive the actuator and/or move the cantilevered optical fiber. One way is to drive the actuator with constant frequency actuator drive signal. The constant frequency is generally at or very near the resonant frequency of the cantilevered optical fiber.

Figure 3:
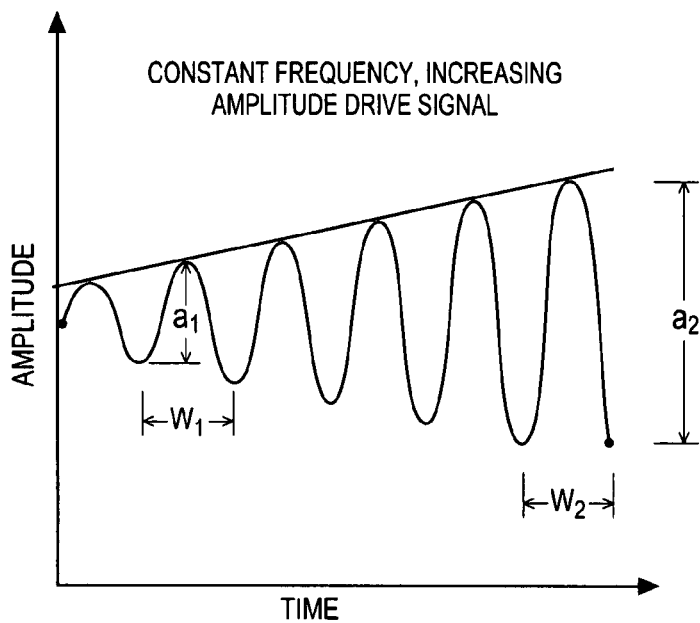
FIG. 3 is a graph showing a constant frequency, increasing amplitude actuator drive signal.

FIG. 3 is a graph showing a constant frequency, increasing amplitude actuator drive signal. Time is plotted on the horizontal axis, versus amplitude on the vertical axis.

The actuator drive signal has periodic shape, in this particular case a sinusoidal or sine wave shape. The sinusoid has a repeating pattern of peaks. The number of peaks per unit time is the frequency of the signal. In the illustrated drive signal, the frequency is constant. The frequency of the sine wave is inversely proportional to the wavelength or spacing between adjacent peaks. Since the frequency is constant, the wavelength is also constant. As shown, an initial first wavelength (w1) is equal to a final second wavelength (w2).

The heights of the peaks are the amplitudes of the drive signal. Notice that the amplitude of the drive signal increases over time. Initial first amplitude (a1) is less than final second amplitude (a2). The amplitude may correspond to the voltage of an actuator drive signal.

Figure 4:
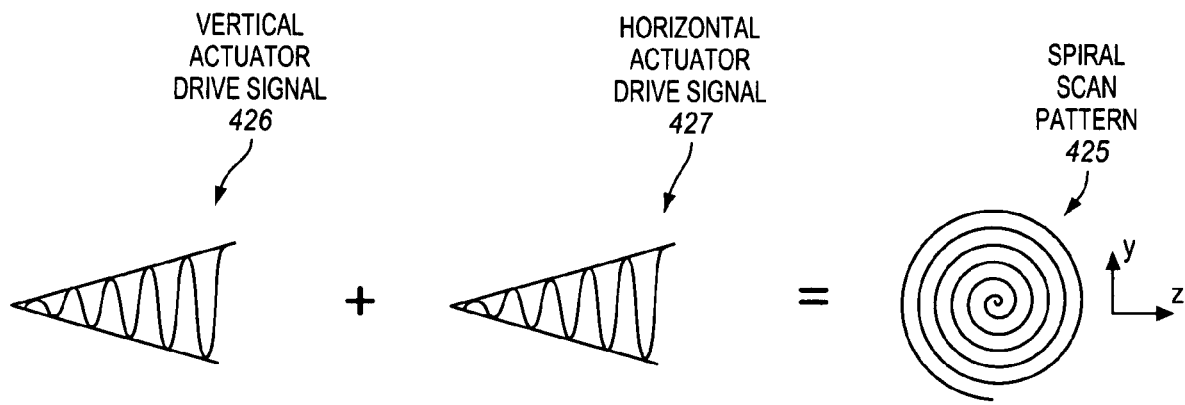
FIG. 4 shows a pair of out-of-phase, constant frequency, increasing amplitude actuator drive signals that may be applied to four quadrant electrodes of an actuator of a scanning fiber device similar to that show in FIG. 2 in order to scan a cantilevered optical fiber in a spiral scan pattern.

FIG. 4 shows a pair of out-of-phase, constant frequency, increasing amplitude actuator drive signals that may be applied to the four quadrant electrodes of an actuator of a scanning fiber device similar to that show in FIG. 2 in order to scan a cantilevered optical fiber in a spiral scan pattern 425. The pair of drive signals include a vertical actuator drive signal 426 ($y=a_1*\sin(\omega t+\phi)$), and a horizontal actuator drive signal 427 ($z=a_2*\cos(\omega t)$). In these equations, where a1 and a2 are potentially different amplitudes, $\omega$ is $2*\pi*f$, f is frequency, t is time, and $\phi$ is a phase shift.

The actuator drive signals each have constant and equal frequency, and increasing amplitude. In the case of a circular cross-section optical fiber, the horizontal and vertical actuator drive signals will have the same frequency. Typically, the horizontal and vertical actuator drive signals are about 90° out-of-phase. In a real system the amplitudes may be unequal and the phase difference may differ from 90° out-of-phase. The "diameter" of the spiral increases as the amplitudes of the drive signals increase. The maximum diameter generally coincides with the maximum amplitudes.

FIG. 5 conceptually illustrates that oversampling may occur in the center portions of a spiral scan pattern generated with constant frequency, increasing amplitude actuator drive signals like those shown in FIG. 4 if backscattered light from the illumination spot is sampled at a constant rate. If the frequency (or number of revolutions per unit time) of the cantilevered optical fiber is constant, then the velocity of the cantilevered optical fiber may be less in the center of the spiral (where the spiral diameter is smaller) than in the outer turns of the spiral (where the spiral diameter is larger). As a result, if backscattered light from the illumination spot is sampled at a constant rate, then significantly more points may be sampled per unit length of the spiral in the center portions of the spiral than in the outer turns or peripheral portions of the spiral.

In the illustration, dots are used to conceptually represent sampling positions. Notice that there are more dots per unit length in the center than in the outer turns. In practice, the amount of oversampling in the center may be tens or hundreds of times more than the sampling in the outer turns, although this may depend upon the size of the spiral and other factors. The oversampled points or positions in the center may be averaged to reduce noise but are sometimes simply discarded. In some implementations, it may be advantageous to more evenly distribute these sampling positions throughout the spiral scan pattern. For similar reasons, in a scanning beam image display device, the slower velocity of the optical fiber in the center portion of the spiral may tend to result in brightening of the center portion of the image for a constant pixel sample rate due to the increased number of modulated illumination spots in the center portion.

FIG. 6 is a graph of resonant gain characteristics of a cantilevered optical fiber operated in a first mode of resonance. Frequency of vibration of the cantilevered optical fiber is plotted on the horizontal axis versus displacement or deflection of the free distal end of the cantilevered optical fiber on the vertical axis.

The displacement increases around, and peaks at, a mechanical or vibratory resonant frequency. This is due to an increase in the resonant gain of the cantilevered optical fiber. In the illustration, the displacement has a relatively Gaussian dependency on frequency, with the greatest displacement occurring at the resonant frequency. In practice, there may be significant deviation from such a Gaussian dependency, although the displacement still typically peaks at the resonant frequency.

In practice, the optical fiber is generally vibrated at or around, for example within a Q-factor of, its resonant frequency, or harmonics of the resonant frequency. As is known, the Q-factor is the ratio of the height of the resonant gain curve to the width of the curve. Due to the increased resonant gain, this may help to reduce the amount of energy, or magnitude of the actuator drive signal, needed to achieve a given displacement, or perform a given scan.

However, operating at or around the resonant frequency may put the optical fiber about 90° out-of-phase relative to the phase of the actuator drive signal. This may tend to make the drive signal to position phase relatively sensitive at or around the resonant frequency. In the center portions of the image there is little fiber displacement and distortions due to phase sensitivities may be more noticeable compared to the peripheral portions of the image. As such, slight changes in environmental conditions, which slightly change the resonant frequency, may tend to cause distortions in the center portions of the images constructed when the fiber is vibrated at or very near its resonant frequency. These distortions may be reduced if the frequency of the optical fiber in the center portion of the scan pattern was substantially displaced from the resonant frequency.

Notice from FIG. 6 that merely changing the frequency of the optical fiber may change the displacement, even if the amplitude of the actuator drive signal is constant. In embodiments of the invention, rather than driving the actuator with constant frequency actuator drive signal, the actuator may instead be driven with a variable frequency actuator drive signal.

FIG. 7 is a block diagram of a method 730 of actuating a cantilevered optical fiber of a scanning fiber device, according to embodiments of the invention. The cantilevered optical fiber may be vibrated at an initial frequency that is substantially displaced from a resonant frequency of the cantilevered optical fiber, at block 731. Then, the frequency of vibration of the cantilevered optical fiber may be changed over a period of time toward the resonant frequency, at block 732.

Two different approaches are possible. In a first approach, the initial or starting frequency of the actuator drive signal may be greater than the resonant frequency, and the frequency of the actuator drive signal may be decreased toward the resonant frequency.

Figure 8:
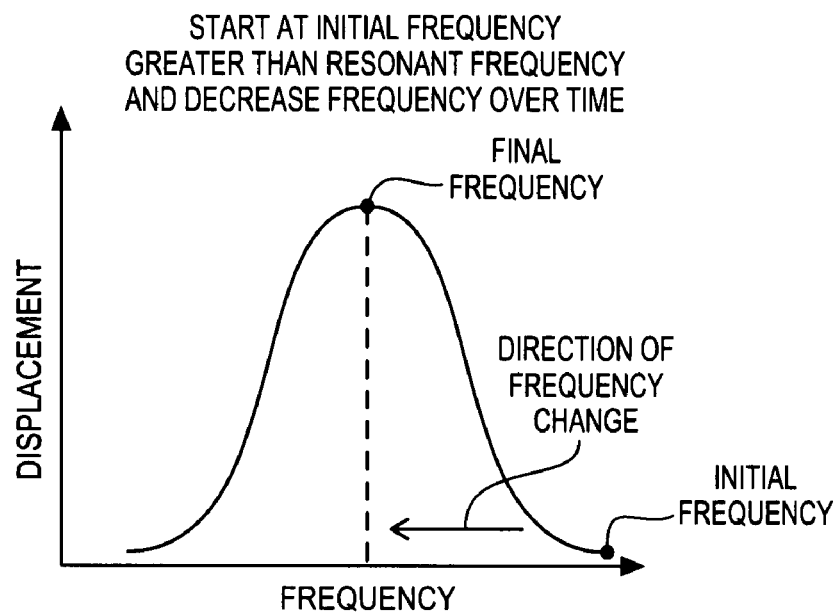
FIG. 8 is a graph showing a first approach for actuating a cantilevered optical fiber, according to embodiments of the invention.

FIG. 8 is a graph showing a first approach for actuating a cantilevered optical fiber, according to embodiments of the invention. The first approach is superimposed on a curve similar to that shown in FIG. 6.

The cantilevered optical fiber may start to move or vibrate at an initial frequency. As shown, the initial frequency is greater than the resonant frequency, and substantially displaced from the resonant frequency. As used herein, the initial frequency is substantially displaced from the resonant frequency if they differ by more than a Q-factor. In alternate embodiments the initial frequency may either be farther from, or closer to, the resonant frequency.

Then, the frequency of vibration of the cantilevered optical fiber may be gradually and continuously decreased over a period of time in a direction toward the resonant frequency until a final or stopping frequency is achieved. As shown, in one or more embodiments of the invention, the final frequency may substantially equal the resonant frequency. Alternatively, the final frequency may be between the resonant frequency and the initial frequency.

As the frequency is decreased toward the resonant frequency, the amount of resonant gain will increase. As a result, the displacement may increase, even if the amplitude of the actuator drive signal used to drive the actuator remains constant, which is not required. Assuming the illustrated Gaussian curve adequately represents the cantilevered optical fiber, then the amount of gain over time may follow the illustrated shape of the curve between the initial and final frequencies, although as previously discussed different optical fibers may be characterized by different resonant gain curves. The increased displacement may be used to scan the optical fiber in a spiral scan pattern, or other expanding scan pattern.

One potential advantage of starting at an initial frequency that is greater than the resonant frequency, and then decreasing the frequency, is a reduction in the oversampling in the center portions of a spiral and certain other scan patterns. In the case of a spiral scan pattern, the greater initial frequency may provide a greater number of revolutions of the cantilevered optical fiber per unit time and hence also a higher velocity of the cantilevered optical fiber in the center portions of the scan compared to if a lower initial frequency were used. This higher velocity may help to more evenly distribute the sampling positions throughout the scan pattern.

Figure 9:
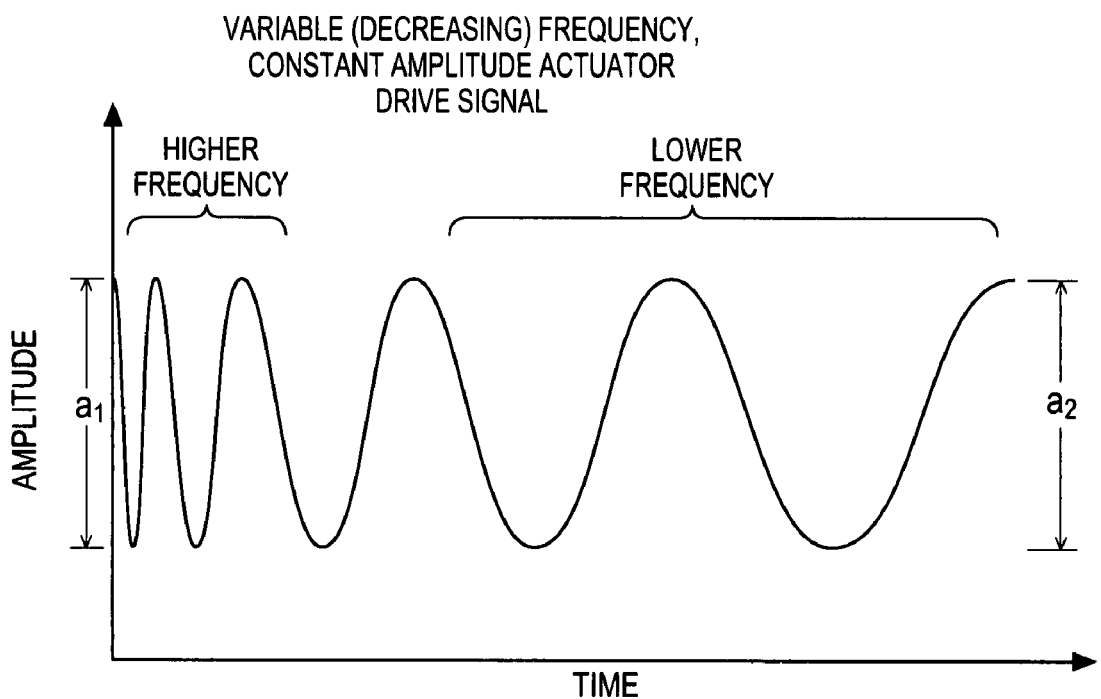
FIG. 9 is a graph showing a variable (decreasing) frequency, constant amplitude actuator drive signal based on the first approach shown in FIG. 8, according to embodiments of the invention.

FIG. 9 is a graph showing a variable (decreasing) frequency, constant amplitude actuator drive signal based on the first approach shown in FIG. 8, according to embodiments of the invention. The graph plots time on the horizontal axis, versus amplitude of the actuator drive signal on the vertical axis.

The actuator drive signal has a periodic or repeating waveform. The particular illustrated waveform is sinusoidal, although this is not required. Examples of suitable non-sinusoidal periodic waveforms, include, but are not limited to, square waves, triangle waves, and sawtooth waveforms, to name just a few examples. The frequency of the actuator drive signal decreases over time. In embodiments of the invention, the initial frequency of the actuator drive signal may be greater than the resonant frequency, and the frequency of the actuator drive signal may decrease in the direction of the resonant frequency. As shown, the signal initially has a higher frequency and finally has a lower frequency.

As shown, in embodiments of the invention, the amplitude or height of the peaks of the variable frequency actuator drive signal may be substantially constant. As used herein, the amplitude is substantially constant if it changes by no more than 10%. By way of example, the drive signal has an initial amplitude (a1) that is equal, or at least substantially equal, to a final amplitude (a2).

In a second approach, the initial frequency of the actuator drive signal may be less than the resonant frequency, and the frequency of the actuator drive signal may be increased toward the resonant frequency.

Figure 10:
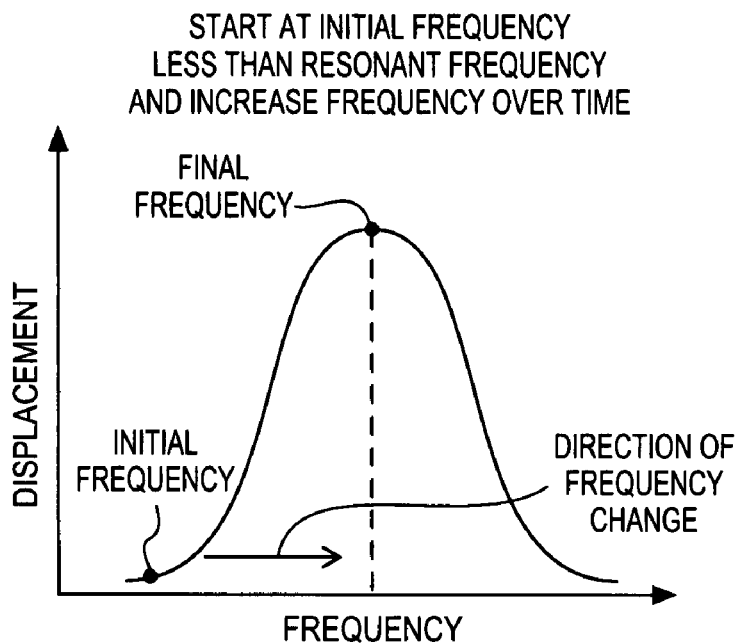
FIG. 10 is a graph showing a second approach for actuating a cantilevered optical fiber, according to embodiments of the invention.

FIG. 10 is a graph showing a second approach for actuating a cantilevered optical fiber, according to embodiments of the invention. In the second approach, the cantilevered optical fiber starts to move or vibrate at an initial frequency that is less than the resonant frequency. Then, the frequency of vibration of the cantilevered optical fiber is increased over a period of time in a direction toward the resonant frequency until a final or stopping frequency is achieved. This is another way to achieve increased displacement, although starting below the resonant frequency may tend to cause more oversampling in the center portion of a spiral scan pattern.

Figure 11:
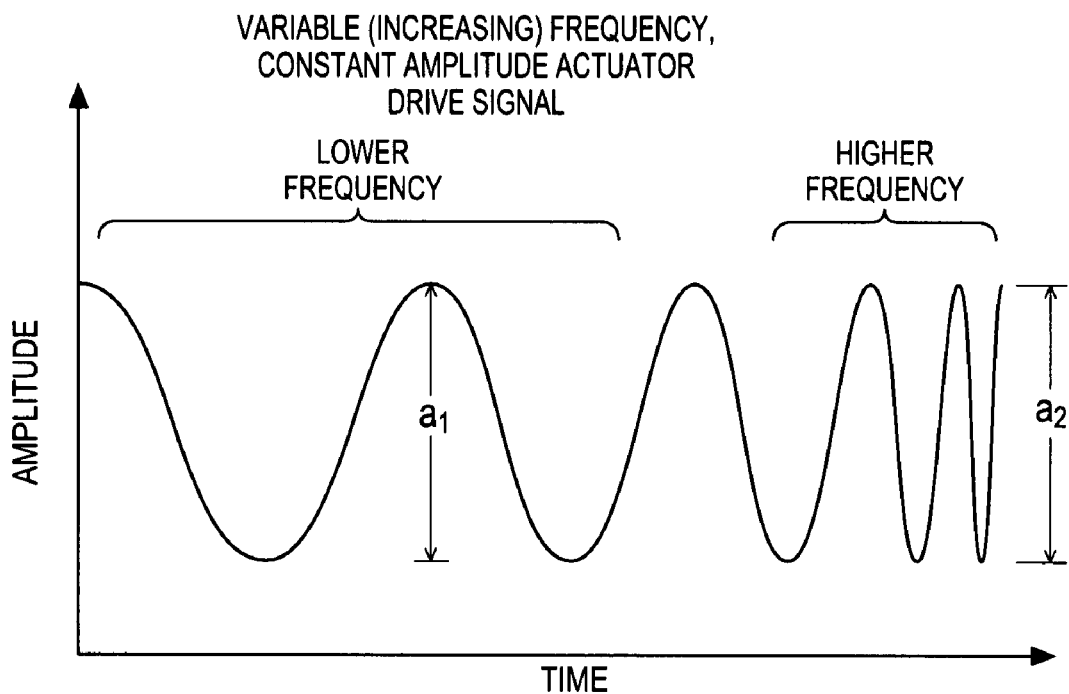
FIG. 11 is a graph showing a variable (increasing) frequency, constant amplitude actuator drive signal based on the second approach shown in FIG. 10, according to embodiments of the invention.

FIG. 11 is a graph showing a variable (increasing) frequency, constant amplitude actuator drive signal based on the second approach shown in FIG. 10, according to embodiments of the invention. In this actuator drive signal, the frequency increases over time. In embodiments of the invention, the initial frequency may be less than the resonant frequency, and the frequency of the actuator drive signal may increase in the direction of the resonant frequency.

Otherwise, the second approach may have similar variations or alternatives as the previously described first approach. These will not be repeated to avoid obscuring the description.

Different ways of changing the frequency of the cantilevered optical fiber and/or the actuator drive signal over time are possible. In one or more embodiments the rate of change of the frequency may be substantially constant. Alternatively, in one or more embodiments, the rate of change of the frequency may be substantially non-constant.

Figure 12:
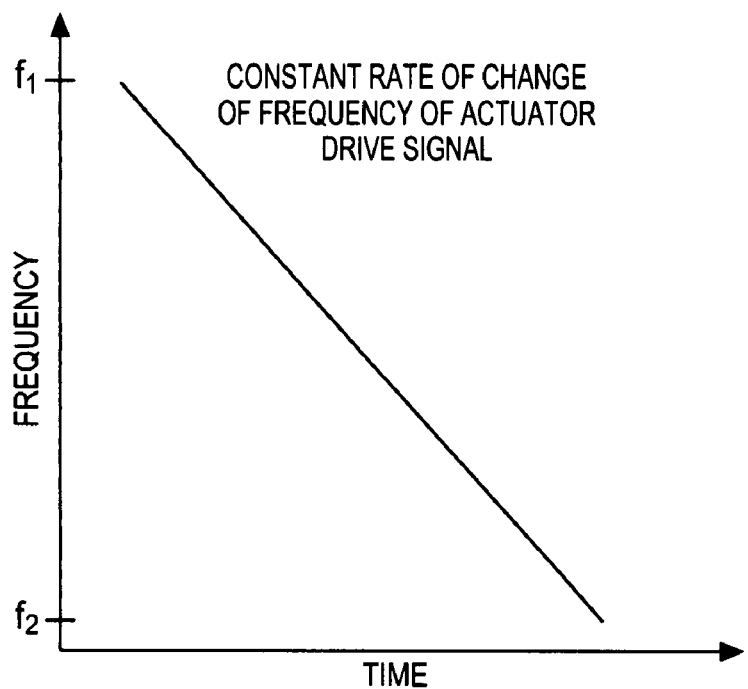
FIG. 12 is a graph showing that a rate of change of a frequency of a cantilevered optical fiber and/or an actuator drive signal may be substantially constant over a period of time, according to embodiments of the invention.

FIG. 12 is a graph showing that a rate of change of a frequency of the cantilevered optical fiber and/or the actuator drive signal may be substantially constant over a period of time, according to embodiments of the invention. The graph plots time on the horizontal axis, versus frequency on the vertical axis.

In the illustration, the frequency decreases linearly from an initial frequency (f1) to a final frequency (f2). In alternate embodiments, the frequency may increase linearly. The linearity implies that the rate of change of the frequency is constant, or at least substantially constant. As used herein, the rate of change of the frequency is substantially constant if the rate changes by no more than 10%.

In the particular case of a spiral scan pattern, a constant rate of change of the frequency may in some cases tend to result in relatively more turns of the spiral in the center and outer portions of the spiral, and relatively fewer turns of the spiral in the intermediate middle portion of the spiral. With quick reference to the Gaussian curve shown in FIG. 8, it is readily seen that it is in this intermediate middle portion where the displacement increases most rapidly with changing frequency (i.e., has the steepest slope). Since the displacement increases more rapidly in this intermediate middle portion, if a constant rate of change of the frequency is used, then the spiral diameter may increase more rapidly in this intermediate middle portion. In some cases it may be desirable if the spacing of the turns of the spiral was equal, or at least more equal.

Figure 13:
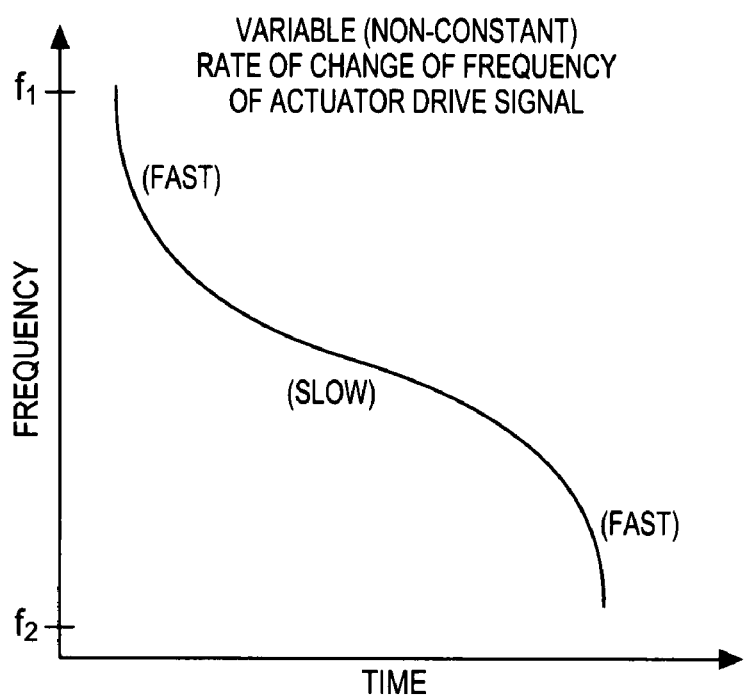
FIG. 13 is a graph showing that a rate of change of a frequency of a cantilevered optical fiber and/or an actuator drive signal may be substantially non-constant or substantially changing over a period of time, according to embodiments of the invention.

FIG. 13 is a graph showing that a rate of change of a frequency of the cantilevered optical fiber and/or the actuator drive signal may be substantially non-constant or substantially changing over a period of time, according to embodiments of the invention. In the illustration, the frequency has a curvilinear decrease over time. Alternatively, the frequency may have a curvilinear increase over time.

As shown, in one or more embodiments, the curvilinear dependency may include a fast initial rate of change near an initial frequency (f1), followed by an slow intermediate rate of change, followed by a fast final rate of change near a final frequency (f2). Notice that the relative rates of change of the frequency are opposite or inverted relative to the change in displacement versus frequency between the initial and final frequencies shown in the curve of FIG. 8. That is, the changes in FIG. 8 are slow near the initial frequency, then fast, and then slow again near the final frequency. As previously mentioned, some optical fibers may deviate from FIG. 8, in which case the change in the frequency may also deviate from the illustrated curvilinear dependency.

By way of example, such opposite or inverted rates of change may help to more evenly distribute the number of turns or more evenly space the turns in the center, intermediate, and outer portions of a spiral scan pattern. Accordingly, in one or more embodiments of the invention, the rate of change of the frequency of a cantilevered optical fiber and/or an actuator drive signal may be changed or varied to obtain a desired spacing, for example a substantially equal spacing, of the turns of the spiral. Other reasons for using non-constant or curvilinear rates of change, including for non-spiral scan patterns, are also contemplated.

Figure 14:
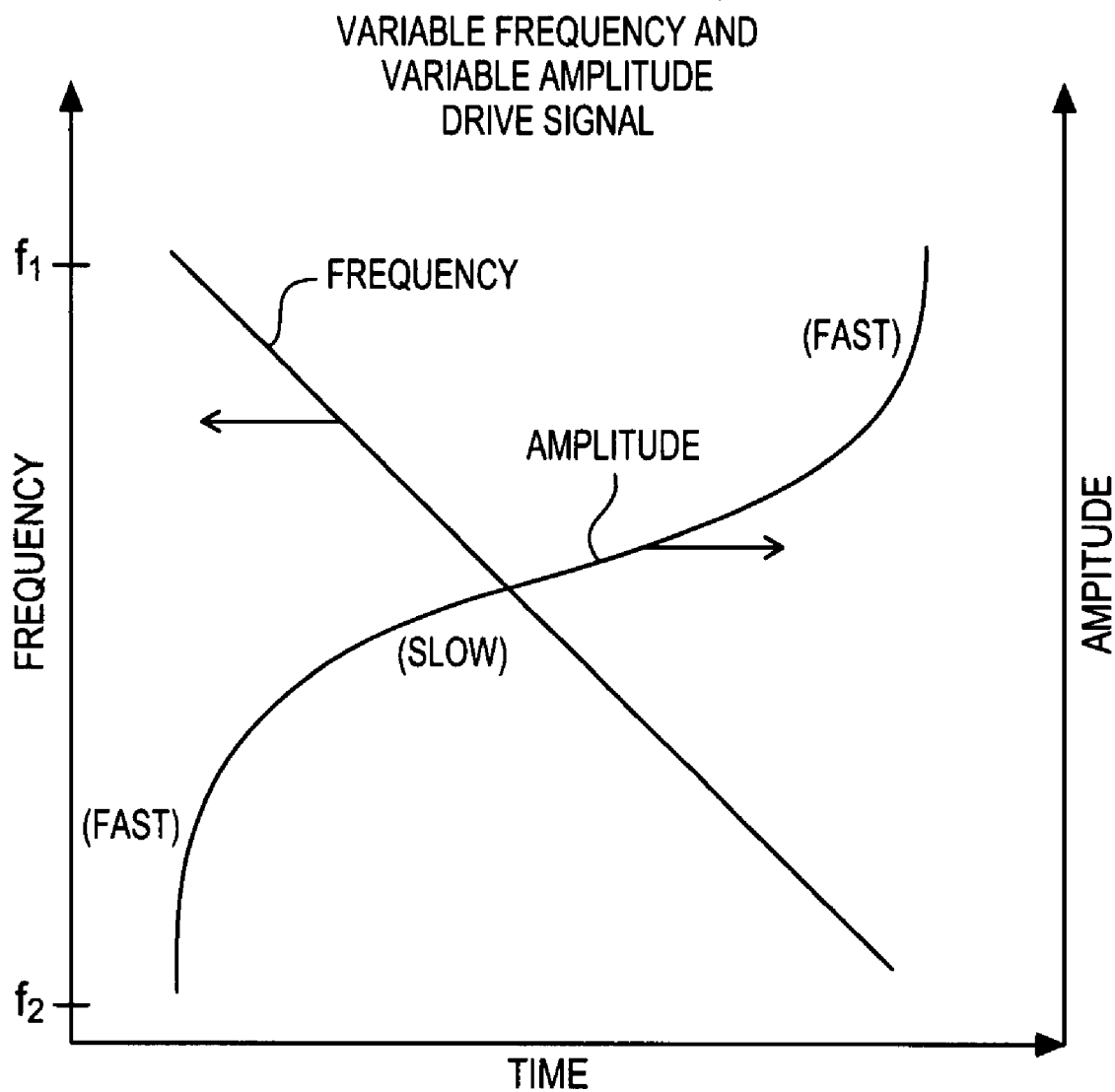
FIG. 14 is a graph showing that both a frequency and amplitude of an actuator drive signal may vary over time, according to embodiments of the invention.

FIG. 14 is a graph showing that both a frequency and amplitude of an actuator drive signal may vary over time, according to embodiments of the invention. The graph plots time on the horizontal axis, versus frequency on the left vertical axis and amplitude on the right vertical axis.

In this particular illustrative example, the frequency has a substantially constant rate of change (decrease) over time. The amplitude has a curvilinear increase over time. In particular, the amplitude has a fast initial increase near an initial time corresponding to an initial frequency (f1), followed by an slow intermediate increase, followed by a fast final increase near a final time corresponding to a final frequency (f2). By way of example, the amplitude, rather than the frequency, may be used to help more evenly distribute the number of turns or more evenly space the turns in the center, intermediate, and outer portions of a spiral scan pattern.

In other embodiments, the frequency change may be non-linear and the amplitude change may be linear or curvilinear. In still other embodiments, both the frequency and amplitude changes may be non-linear or curvilinear. In general, the ability to vary both the frequency and amplitude of the actuator drive signal may afford more control over the shape of the scan pattern.

Recall that sometimes two or more different actuator drive signals may be applied to the same actuator tube. Generally the rate of change of the frequency of each of the different actuator drive signals should be the same. However, in one or more embodiments, the amplitudes of the different actuator drive signals and/or the rates of change of the different amplitudes may potentially be unequal or different.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the configurations, functions, and manner of operation, of the components of the embodiments. All equivalent relationships to those illustrated in the drawings and described in the specification are encompassed within embodiments of the invention. The scope of the invention is not to be determined by the specific examples provided above but by the claims below.

The terms "coupled" and "connected," along with their derivatives, are used herein. These terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other physically, electrically, or optically.

In the description and claims, the term "scanning" in "scanning fiber device", "scanning fiber system", and the like, does not necessarily imply that the device is in use, or presently in the process of scanning. Rather, the term scanning merely implies that the device is capable of scanning.

Various operations and methods have been described. The methods have been described in a basic form, but operations may optionally be added to the methods. In some cases, operations may be removed from the methods. In some cases, the operations of the methods may be performed in different order. Many modifications and adaptations may be made to the methods and are possible and contemplated.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
    vibrating a cantilevered optical fiber at an initial frequency that is substantially displaced from a resonant frequency of the cantilevered optical fiber;
    changing the frequency of vibration of the cantilevered optical fiber over a period of time toward the resonant frequency;
    directing light through an end of the cantilevered optical fiber over the period of time while the cantilevered optical fiber is vibrated; and
    constructing an image based on the light directed through the end of the cantilevered optical fiber over the period of time while the cantilevered optical fiber is vibrated at the initial frequency that is substantially displaced from the resonant frequency and the frequency of the vibration is changed over the period of time toward the resonant frequency.

2. The method of claim 1, wherein the initial frequency is greater than the resonant frequency, and wherein changing the frequency comprises decreasing the frequency.

3. The method of claim 1, wherein the initial frequency is less than the resonant frequency, and wherein changing the frequency comprises increasing the frequency.

4. The method of claim 1, wherein a rate of change of the frequency is substantially constant over the period of time.

5. The method of claim 1, wherein a rate of change of the frequency is substantially non-constant over the period of time.

6. The method of claim 1, further comprising moving the cantilevered optical fiber in an expanding scan pattern.

7. The method of claim 6, wherein the expanding scan pattern comprises a spiral scan pattern.

8. The method of claim 7, wherein a rate of change of the frequency changes over the period of time to make spacing of turns in the spiral scan pattern more even.

9. The method of claim 1, wherein said vibrating the cantilevered optical fiber and said changing the frequency of vibration of the cantilevered optical fiber are performed responsive to receiving at least one variable frequency actuator drive signal at an actuator that is coupled with the cantilevered optical fiber.

10. The method of claim 1, further comprising inserting the cantilevered optical fiber into a patient before said vibrating and said changing.

11. The method of claim 1, wherein changing the frequency of the vibration of the cantilevered optical fiber over the period of time toward the resonant frequency comprises stopping at a frequency that is one of a frequency that is substantially equal to the resonant frequency and a frequency that is between the resonant frequency and the initial frequency.

12. An apparatus comprising: a connector interface to allow a scanning fiber device to be attached; a light source to provide light to the scanning fiber device through the connector interface; and an actuator driver to provide at least one variable frequency actuator drive signal to the scanning fiber device through the connector interface, wherein the variable frequency actuator drive signal has an initial frequency that is substantially displaced from a resonant frequency of a cantilevered optical fiber of the scanning fiber device, and wherein a frequency of the variable frequency actuator drive signal changes over a period of time toward the resonant frequency until a final frequency is achieved, wherein the final frequency comprises one of a frequency that is substantially equal to the resonant frequency and a frequency that is between the resonant frequency and the initial frequency; an image processor to construct an image based on movement of the cantilevered optical fiber of the scanning fiber device over the period of time the frequency of the variable frequency actuator drive signal changes toward the resonant frequency until the final frequency is achieved.

13. The apparatus of claim 12, wherein the initial frequency is greater than the resonant frequency, and wherein the frequency decreases over the period of time.

14. The apparatus of claim 12, wherein the initial frequency is less than the resonant frequency, and wherein the frequency increases over the period of time.

15. The apparatus of claim 12, wherein a rate of change of the frequency is substantially constant over the period of time.

16. The apparatus of claim 12, wherein a rate of change of the frequency is substantially non-constant over the period of time.

17. The apparatus of claim 16, wherein the non-constant rate of change of the frequency is inversely related to a rate of change of a displacement of the cantilevered optical fiber versus the frequency.

18. The apparatus of claim 12, wherein an amplitude of the variable frequency actuator drive signal is substantially constant.

19. The apparatus of claim 12, wherein an amplitude of the variable frequency actuator drive signal is substantially non-constant.

20. The apparatus of claim 19, wherein a rate of change of the amplitude is substantially non-constant over the period of time.

21. The apparatus of claim 12, wherein the apparatus is to construct an image based on the light provided to the scanning fiber device during the period of time.

22. The apparatus of claim 12, wherein the final frequency is between the resonant frequency and the initial frequency.

23. A method comprising:
inserting a cantilevered optical fiber into a patient;
receiving at least one variable frequency drive signal at a piezoelectric tube that is coupled with the cantilevered optical fiber inserted into the patient, wherein the variable frequency drive signal has an initial frequency that is substantially displaced from a resonant frequency of the cantilevered optical fiber, and wherein a frequency of the variable frequency drive signal changes over a period of time toward the resonant frequency;
moving the cantilevered optical fiber in an expanding scan pattern based at least in part on the piezoelectric tube receiving the variable frequency drive signal; and
emitting light from an end of the cantilevered optical fiber while the cantilevered optical fiber is moved in the expanding scan pattern.

24. The method of claim 23, wherein moving the cantilevered optical fiber in the expanding scan pattern comprises moving the cantilevered optical fiber in a spiral scan pattern, and wherein a number of revolutions of the cantilevered optical fiber per unit time changes over the period of time.

25. The method of claim 23, wherein receiving the drive signal comprises receiving a drive signal that has an initial frequency that is greater than the resonant frequency.

26. The method of claim 23, wherein receiving the drive signal comprises receiving a drive signal having a rate of change of frequency that is substantially constant over the period of time.

27. The method of claim 23, wherein receiving the drive signal comprises receiving a drive signal having a rate of change of frequency that is substantially non-constant over the period of time.

28. The method of claim 23, wherein receiving the drive signal comprises receiving a drive signal that has a substantially constant amplitude.

29. The method of claim 23, wherein receiving the drive signal comprises receiving a drive signal that has a substantially non-constant amplitude.

30. A method comprising:
scanning a cantilevered optical fiber of a scanning fiber device in a spiral scan;
changing a number of revolutions of the cantilevered optical fiber per unit time throughout the spiral scan in a direction that increases the resonant gain of the cantilevered optical fiber;
emitting light from an end of the cantilevered optical fiber throughout the spiral scan; and
constructing an image based on the light emitted from the end of the cantilevered optical fiber throughout the spiral scan.

31. The method of claim 30, wherein changing the number of revolutions comprises decreasing the number of revolutions.

32. The method of claim 30, further comprising inserting the cantilevered optical fiber into a patient before said scanning and said changing.

* * * * *